United States Patent [19]

van Duyn

[11] Patent Number: Plant 6,750

[45] Date of Patent: Apr. 25, 1989

[54] ALSTROEMERIA NAMED ELSBETH

[75] Inventor: Cornelius van Duyn, Rijnsburg, Netherlands

[73] Assignee: Groot Associates II, Irvine, Calif.

[21] Appl. No.: 57,233

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the distinctive pink coloration of its blossoms, the petals of which are covered with longitudinal flecks or streaks of a darker shade of pink, white striped margins and a light yellow striped heart. The plant is late in flowering with relatively thick flower stems.

1 Drawing Sheet

BACKGROUND OF THE NEW PLANT

This new Alstroemeria originated as a seedling selected from individual members of breeding stock maintained at Rijnsburg, Holland. The particular seedling was selected by me in 1980 for propagation and testing because of the distinctive coloration of its blossoms produced on upright compact stems. Specifically, the outer and inner petals have pink central areas, white marginal areas and light yellow striped hearts. Both the inner and outer petals have well defined longitudinal streaks or flecks of dark pink, such streaks of the outer petals being generally limited to their lateral marginal areas. The selected plant was propagated by me at Rijnsburg, Holland through several generations of root divisions to establish that its distinctive characteristics hold true from generation to generation and appear to be firmly fixed.

Breeding efforts commenced in 1978 and propagation is currently being carried out at Rijnsburg, Holland. The nearest variety is the Alstroemeria called Lione and my new variety, Elsbeth, differs from the Lione variety in that (1) the petals have a darker pink coloration, (2) the flowers are smaller, (3) the plant is later flowering, (4) the flower stems are thicker and (5) the leavers are shorter and rounder.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material, #2107, comprising the ISCC-NBS Centroid Color Charts and NBS Special Publication, #440.

THE PLANT

Origin: Seedling.
Parentage: Seed parent.
Classification: Alstroemeria hybrid.
Form: A generally erect bush having an upright stalk with flower-bearing branches in simple umbel arrangement at its top.
Height: About 1.1 meters.

Growth: Upright and vigorous.
Root stock: Tuberous.
Foliage:
- *Quantity.*—Abundant.
- *Number of leaves.*—About 20–25 per stem.
- *Size of leaf.*—About 11.0×2.0 cm.
- *Shape of leaf.*—Parallel venation.
- *Texture.*—Smooth.
- *Color.*—Upper side: Dark green. Under side: Dark green.

THE BUD

Form: Long, pear shaped.
Size: Large.
- *Diameter.*—About 1.2 cm.
- *Length.*—About 3.5 cm.

Peduncle:
- *Length.*—About 12 cm.
- *Texture.*—Smooth.
- *Form.*—Erect.

THE FLOWER

Blooming habit: Profusely during late season in Spring.
Flower size: Medium.
- *Diameter.*—About 4.5 cm.
- *Depth.*—About 5.5 cm.

Borne: Terminal clusters.
Shape: Generally cup shaped with petals tips curling outwardly.
Petalage:
- *Number of petals.*—Six.
- *Arrangement.*—Two concentric circles of three.
- *Form.*—Broad oval.
- *Texture.*—Soft.
- *Appearance.*—Velvety.

Color:
- *Outer petals.*—Light grayish purple (No. 258) with light pink (No. 252) margins and green pigmentations at the petal tips.
- *Inside petals.*—Light pink (No. 252) with white (No. 263) margins and a light yellow (No. 86) heart. All petals have numerous generally longitudinal stripes or flecks of deep purple (No. 260).

p0 Persistence: The flowers hang on and dry.
Main stem or stalk:
- *Length.*—About 12 cm.
- *Color.*—Green.
- *Character.*—Strong and upright.

Lasting quality of flower: About three weeks. As a cut flower, about 10–14 days.

REPRODUCTIVE ORGANS

Stamens:
*Number.*—Six.
*Arrangement.*—One opposite each petal.
Anthers:
*Size.*—About 6 cm×0.2 cm.
*Color.*—Yellowish green (No. 120).
Filaments:
*Length.*—About 2.8 cm.
*Color.*—Pink (No. 250).
Pollen.—Brownish gray.
Pistils:
*Number.*—One.
*Styles.*—Length: About 2.8–3.2 cm. Color: Light pink.

Fruit:
*Shape.*—Round.
*Color.*—Light brown.

This plant is particularly noted for the distinctive coloration of its flowers, which coloration does not clearly resemble that of any other Alstroemeria plant previously known to me. The deepish reddish brown flecks on the light grayish purple (central) and white (margins) background with the strong yellow striped heart make this plant an attractive addition to the Alstroemeria family.

I claim:

1. A new and distinctive Alstroemeria cultivar, substantially as herein shown and described, characterized by the distinctive coloration of its medium and profusely blooming flowers.

* * * * *

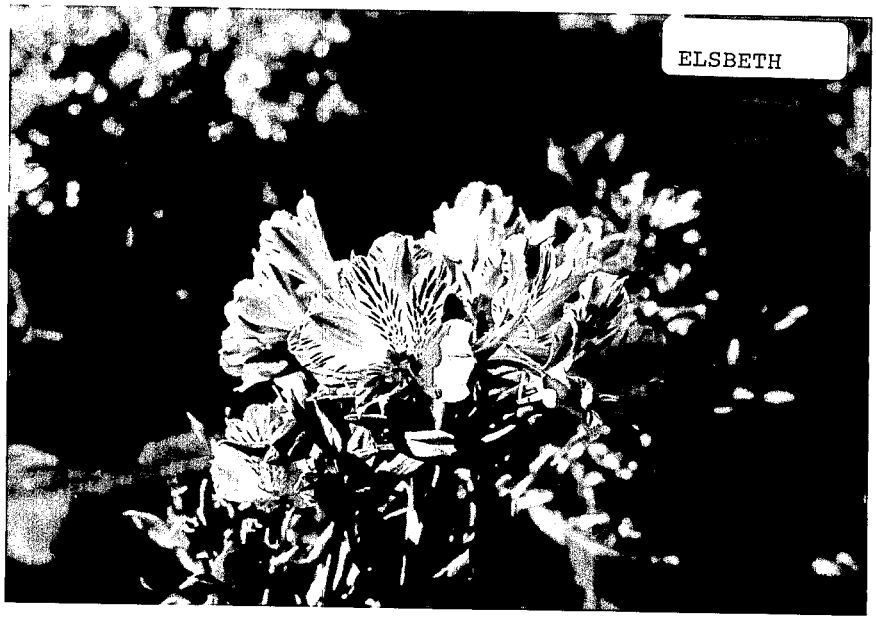
ELSBETH